United States Patent
Yamane

(10) Patent No.: US 8,696,553 B2
(45) Date of Patent: Apr. 15, 2014

(54) AUTOMATIC RETRACTABLE SYRINGE

(75) Inventor: Kenji Yamane, Saitama (JP)

(73) Assignee: FUJIFILM Corporation, Tokyo (JP)

( * ) Notice: Subject to any disclaimer, the term of this patent is extended or adjusted under 35 U.S.C. 154(b) by 1091 days.

(21) Appl. No.: 12/372,432

(22) Filed: Feb. 17, 2009

(65) Prior Publication Data

US 2009/0209823 A1 Aug. 20, 2009

(30) Foreign Application Priority Data

Feb. 18, 2008 (JP) ................................. 2008-035847

(51) Int. Cl.
*A61B 1/12* (2006.01)
*A61M 5/30* (2006.01)
*A61M 5/20* (2006.01)

(52) U.S. Cl.
USPC .............. 600/158; 600/159; 604/68; 604/135

(58) Field of Classification Search
USPC ............. 600/158, 568, 565, 159; 604/68, 135
See application file for complete search history.

(56) References Cited

U.S. PATENT DOCUMENTS

| | | | | |
|---|---|---|---|---|
| 4,549,554 A | * | 10/1985 | Markham | 600/566 |
| 4,572,210 A | * | 2/1986 | McKinnon | 600/578 |
| 4,576,650 A | * | 3/1986 | Yabe et al. | 134/22.12 |
| 4,664,128 A | * | 5/1987 | Lee | 600/566 |
| 4,667,691 A | * | 5/1987 | Sasa | 134/169 C |
| 5,395,345 A | | 3/1995 | Gross | |
| 2005/0096504 A1 | | 5/2005 | Akiba | |

FOREIGN PATENT DOCUMENTS

| | | |
|---|---|---|
| EP | 1 882 442 A1 | 1/2008 |
| JP | 7-265260 A | 10/1995 |
| JP | 2000-279871 A | 10/2000 |
| JP | 2003-135391 A | 5/2003 |
| JP | 2003-172250 A | 6/2003 |
| WO | WO-00/29052 A1 | 5/2000 |

* cited by examiner

*Primary Examiner* — Alireza Nia
(74) *Attorney, Agent, or Firm* — Birch, Stewart, Kolasch & Birch, LLP

(57) ABSTRACT

An automatic retractable syringe includes a tubular body on which a syringe opening is provided; a piston body in whose pressing portion a vent hole $V_A$ is formed and in whose shaft portion a vent passage passing from the vent hole $V_A$ through inside to the front end portion is formed; and a spring which returns the pressed piston body to its original position. When the pressing portion is pressed by a thumb or other finger plugging the vent hole $V_A$ to move the piston body forward, air is supplied from the syringe opening. Subsequently, when the thumb or other finger is released, air flows into the tubular body through the vent hole $V_A$ and the vent passage, and the piston body automatically returns to its original position by the spring. Therefore, air can be consecutively supplied by repeatedly pressing the pressing portion.

5 Claims, 5 Drawing Sheets

AUTOMATIC RETRACTABLE SYRINGE

BACKGROUND OF THE INVENTION

The disclosure of Japanese Patent Application No. 2008-035847, filed on Feb. 18, 2008, including its specification, claims and drawings, is incorporated herein by reference in its entirety.

FIELD OF THE INVENTION

The present invention relates to an automatic retractable syringe, and more particularly to a configuration of a syringe which is used to supply air or water using an air supply/water supply tube provided particularly in an endoscope or the like and can be carried as an air supply/water supply device.

DESCRIPTION OF THE RELATED ART

FIG. 5 illustrates a configuration of a conventional endoscope apparatus (see Japanese Patent Laid-Open No. 2003-135391). The endoscope (scope) has, for example, a front end portion 1A provided with a solid state image pickup element, an operation portion 1B provided through a curved portion, and the like. This endoscope includes an air supply/water supply tube 3a for cleaning an observation window disposed on a front end surface thereof, a water supply tube 3b and an air supply tube 3c branched off from the air supply/water supply tube 3a. The operation portion 1B includes an air supply/water supply button 4a for switching between the water supply tube 3b and the air supply tube 3c, and controlling air supply and water supply.

In addition, the above water supply tube 3b connects to an air supply/water supply pump 8 through a water supply tank 6 storing cleaning water, and the air supply tube 3c directly connects to the air supply/water supply pump 8. Moreover, this operation portion 1B further includes a suction button 4b and a camera shutter release button 4c, as well as a forceps opening 5 for introducing a treatment tool into a treatment tool insertion channel disposed in the endoscope, and the like.

According to such an endoscope apparatus, when the air supply/water supply button 4a is operated (e.g., pressed to the second position) to supply water, the air supply tube 3c is closed and the water supply tube 3b is in an open state. Then, the cleaning water inside the water supply tank 6 is sprayed from a nozzle on the front end surface toward the observation window. When it is operated (e.g., pressed to the first position) to supply air, the water supply tube 3b is closed and the air supply tube 3c is in an open state. Then, air is supplied from the pump 8 in the same manner. Such water supply and air supply remove contamination and the like attached to the observation window, thereby maintaining a good observed state of an object to be observed. It should be noted that the above description uses an example of a mechanical valve, but an electric button (switch) and an open/close valve may be used to supply air and water.

However, as described above, the conventional endoscope apparatus requires the air supply/water supply pump (device) 8 to supply air and water, and thus has a problem in that it is difficult to use the endoscope in a place other than a facility provided with the air supply/water supply pump 8.

A portable endoscope apparatus can be used in a various kinds of places other than a well-equipped facility, at bedside, and in emergency. In addition, a simplified configuration thereof leads to reduced costs. Therefore, a portable and simplified device for air supply and water supply can provide a highly convenient endoscope apparatus.

Moreover, a widely used syringe allows air or water to be supplied once at a time by manually pressing the piston, but an unlimited amount of air or water cannot be supplied in an easy and consecutive manner.

In view of the above problems, the present invention has been made, and an object of the present invention is to provide an automatic retractable syringe for an endoscope capable of providing a simplified and portable device for supplying air or water leading to a portable and simplified automatic retractable syringe and endoscope apparatus capable of supplying an unlimited amount of air or water in an easy and consecutive manner.

SUMMARY OF THE INVENTION

In order to achieve the above object, the automatic retractable syringe in accordance with the present invention is characterized by being configured to include a tubular body on whose front end portion a syringe opening (injection opening) is provided; a piston body in which a vent passage passing from a vent hole of a pressing portion through inside to a front end portion is formed and which reciprocates inside the tubular body; and a spring which is disposed between the piston body and the tubular body, and returns the pressed piston body to its original position.

In addition, the piston body can include a discoid piston portion which reciprocates in close contact with an inner surface of the tubular body; a rod-shaped shaft portion which supports the piston portion and whose external diameter is smaller than the internal diameter of the tubular body; and a discoid pressing portion which is disposed at a rear side of the shaft portion so as to move back and forth when pressed with a thumb or other finger.

The spring can be provided between a flange portion provided at a rear side of the tubular body and the pressing portion of the piston body.

Another invention is characterized in that the syringe opening is pipe-connected to an air supply or water supply port of an endoscope so as to use the automatic retractable syringe according to a first aspect of the present invention on the endoscope.

According to the configuration of the present invention, when the pressing portion is pressed by a thumb or other finger plugging the vent hole to move the piston body forward, air is supplied from the syringe opening. Subsequently, when the thumb or other finger is released, air flows into the tubular body through the vent hole and the vent passage and the piston body automatically returns (moves back) to its original position by the spring. Therefore, the operator can consecutively supply air by repeatedly pressing and releasing the pressing portion.

In addition, in the case of an endoscope apparatus, the syringe opening of the automatic retractable syringe can be connected to a water supply tank connected to a water supply tube of the endoscope through a connecting tube or the like. Then, when air is supplied from the syringe opening to the water supply tank, cleaning water or the like can be supplied from the water supply tank through the water supply tube of the endoscope to clean the observation window. Alternatively, when the syringe opening is connected to the air supply port of the air supply tube of the endoscope, air can be supplied from the syringe opening through the air supply tube of the endoscope to dry the observation window.

According to the automatic retractable syringe of the present invention, an unlimited amount of air or water can be supplied in an easy and consecutive manner by repeating the pressing operation.

In addition, the automatic retractable syringe for an endoscope has an advantage capable of providing a simplified and portable device for air supply or water supply, further a simplified and portable endoscope apparatus, thus allowing the endoscope to be used in a various kinds of places other than a well-equipped facility, at bedside, and in emergency, and thereby providing a highly convenient endoscope apparatus.

DETAILED DESCRIPTION OF THE PREFERRED EMBODIMENTS

Figure 2:
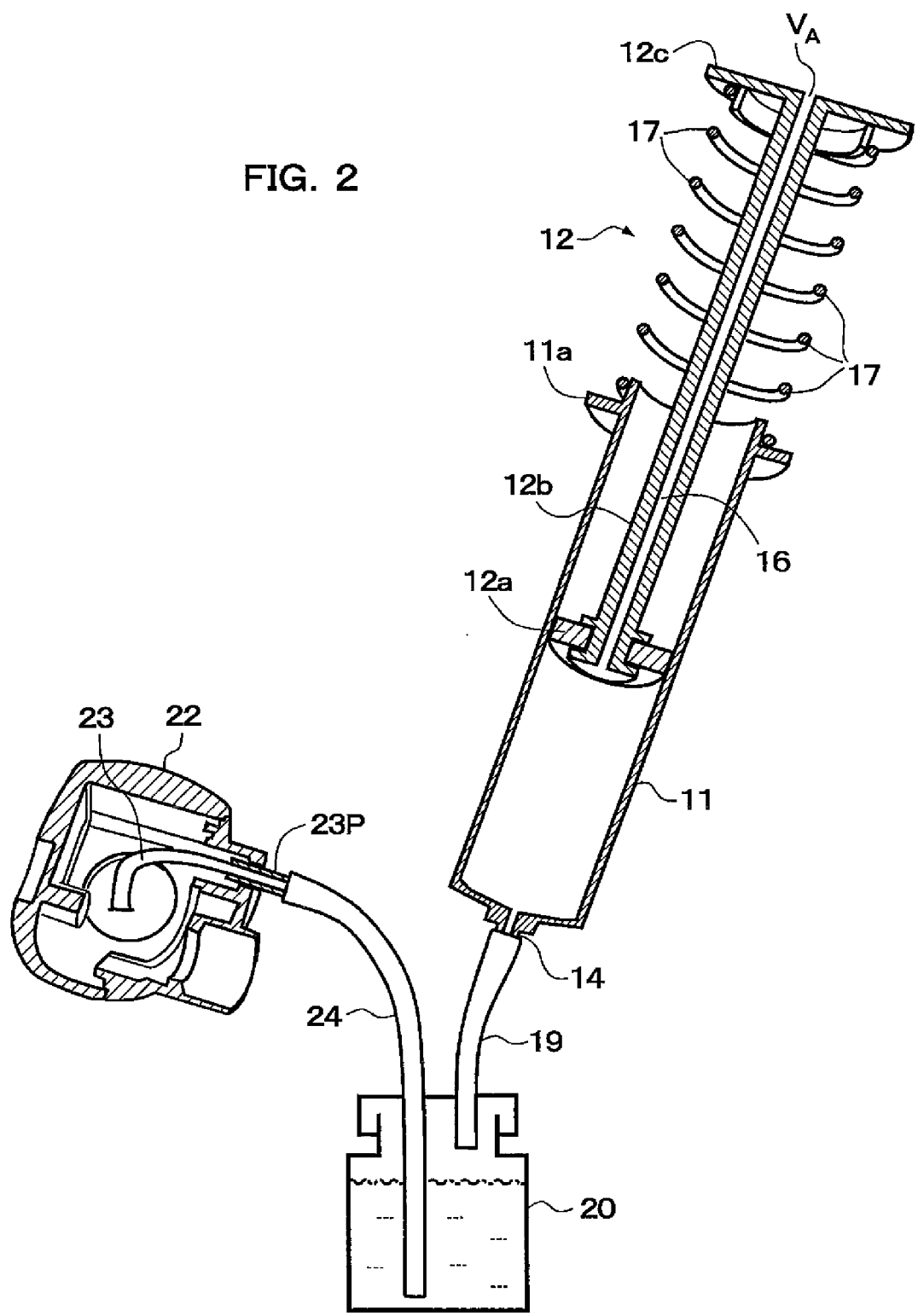
FIG. 2 is a sectional view illustrating a configuration, when not operated, when the automatic retractable syringe for the endoscope of the embodiment is used to supply water.
Figure 3:
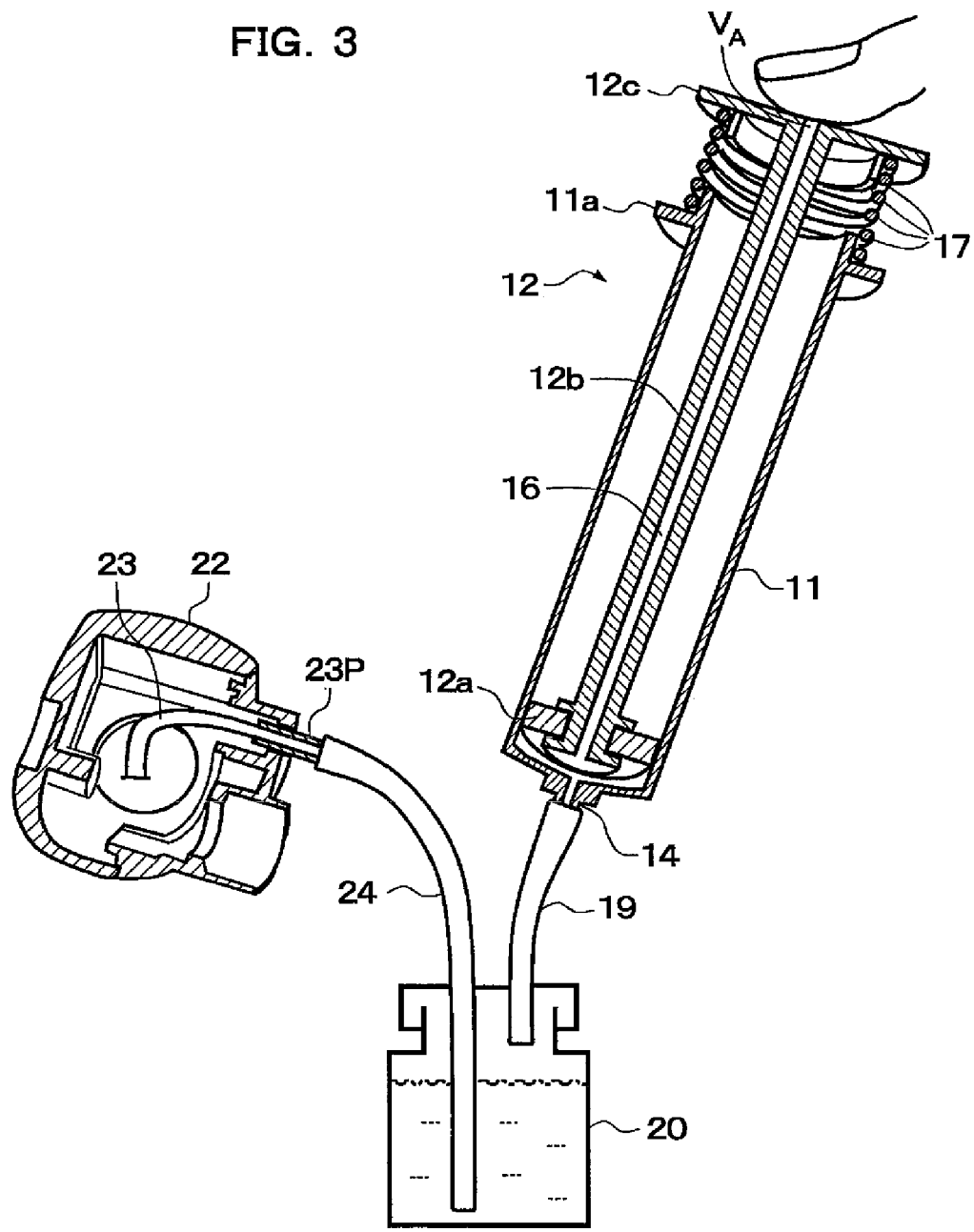
FIG. 3 is a sectional view illustrating a configuration, when pressed, when the automatic retractable syringe for the endoscope of the embodiment is used to supply water.
Figure 4:
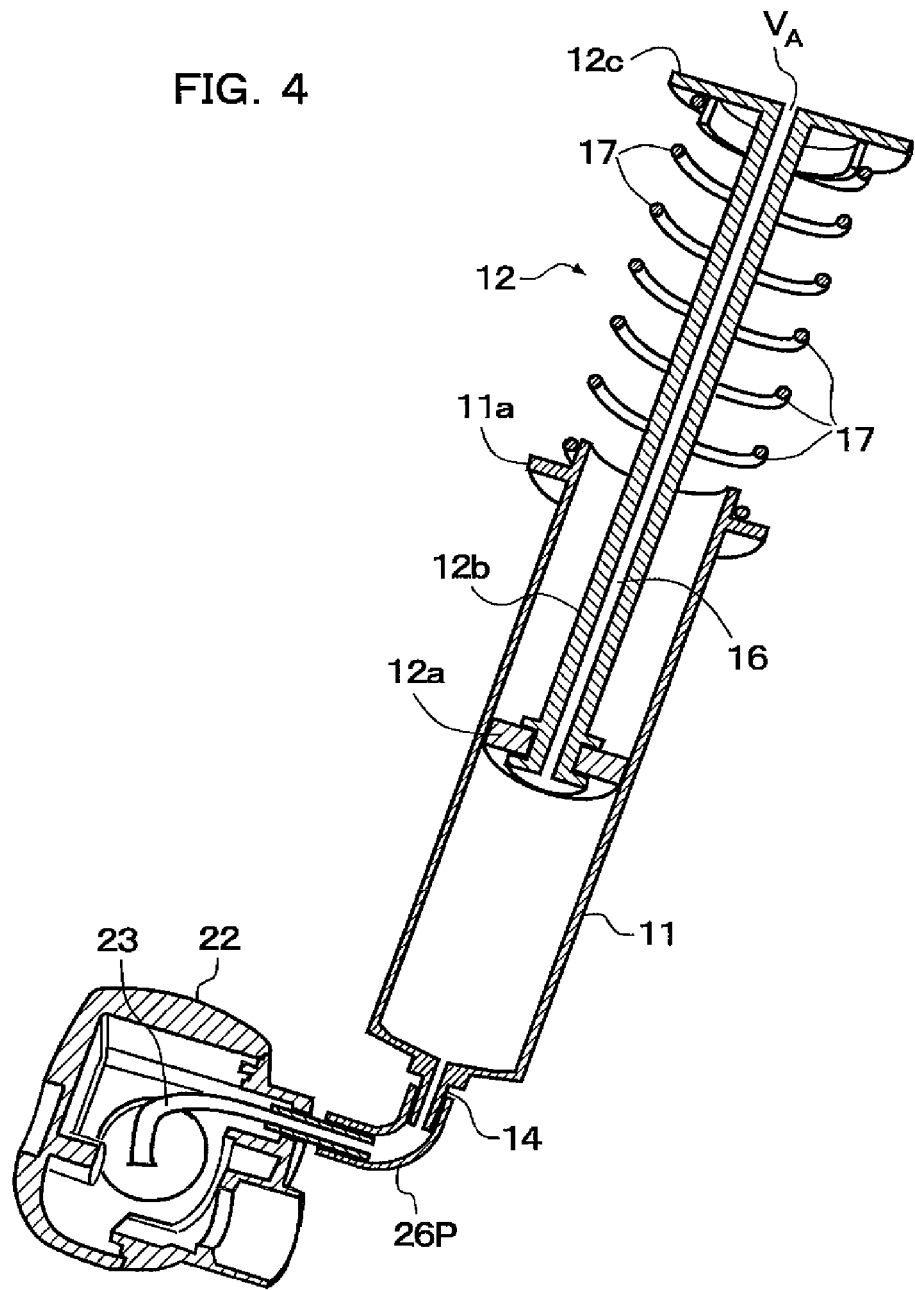
FIG. 4 is a sectional view illustrating a configuration, when not operated, when the automatic retractable syringe for the endoscope of the embodiment is used to supply air.
Figure 5:
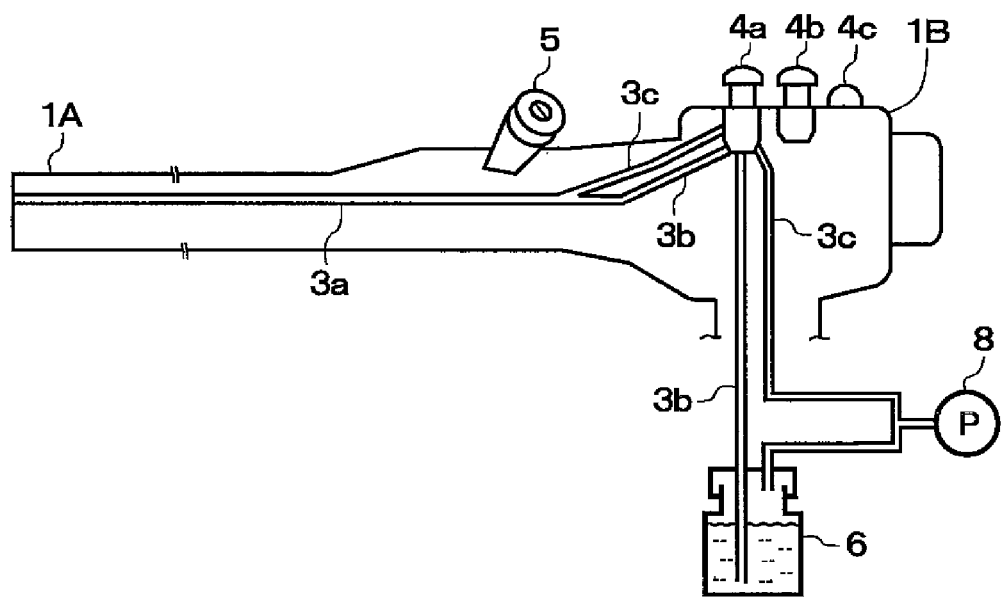
FIG. 5 is a view illustrating a configuration of a conventional endoscope apparatus.

FIG. 1 illustrates a configuration of an automatic retractable syringe in accordance with an embodiment of the present invention. FIGS. 2 to 4 illustrate a configuration of an automatic retractable syringe for an endoscope in accordance with the embodiment. First, as shown in FIG. 1, the syringe of the present embodiment has a cylindrical tubular body 11 and a piston body (slider) 12. The tubular body 11 includes a syringe opening (injection opening) 14 on a front end surface thereof.

On the other hand, the piston body 12 includes a discoid piston portion (sliding portion) 12a with a predetermined thickness which slides (reciprocates) in close contact with an inner surface of the tubular body 11, a cylindrical rod-shaped shaft portion 12b which supports the piston portion 12a and whose external diameter is smaller than the internal diameter of the tubular body 11, and a discoid pressing portion 12c which is disposed at a rear side of the shaft portion 12b so as to move back and forth when pressed with a thumb or other finger. It should be noted that the size (diameter) of the shaft portion 12b may be the same as that of the piston portion 12a.

Moreover, in the piston body 12, a vent hole $V_A$ is formed in a middle portion of the pressing portion 12c, and a shaft portion vent passage (tube path) 16 passing from the vent hole $V_A$ to the front end portion of the shaft portion is formed in the middle of the shaft portion 12b in the radial direction thereof. Further, a spring 17 urging the pressed pressing portion 12c in a direction to its original position is provided (in a state engaged with each other) between a flange portion 11a at the rear side of the tubular body 11 and the pressing portion 12c of the piston body 12. It should be noted that the piston body 12 stops at a position corresponding to the length of the spring 17, but a stopper mechanism for ensuring a reliable and stable stop operation can be provided between the tubular body 11 and the shaft portion 12b.

Figure 1A:
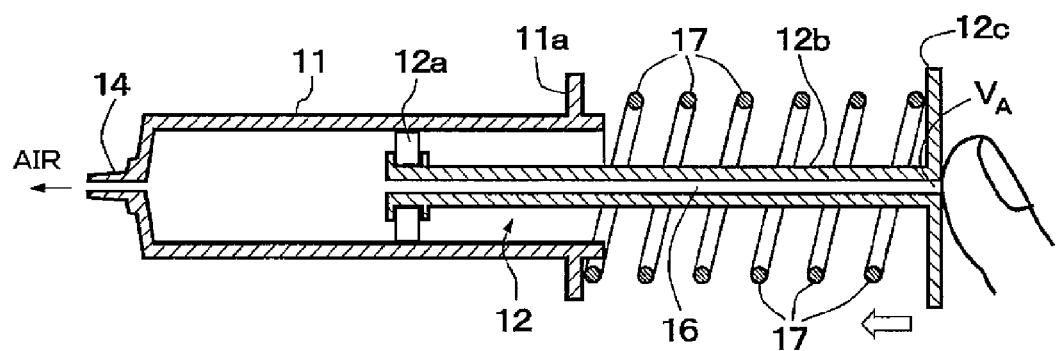
FIG. 1A is a sectional view illustrating a configuration of an automatic retractable syringe, when not operated, in accordance with an embodiment of the present invention.
Figure 1B:
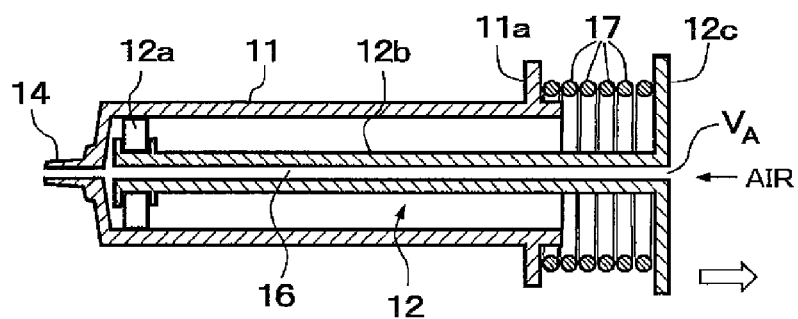
FIG. 1B is a sectional view of the syringe, when pressed, of FIG. 1.

According to such an automatic retractable syringe, in a basic (not operated) state shown in FIG. 1A, when the pressing portion 12c is pressed by a thumb or other finger plugging the vent hole $V_A$ (against the spring 17), air can be supplied by discharging air inside the tube from the syringe opening 14. Then, in a state shown in FIG. 1B, when the finger pressure on the pressing portion 12c is released, the vent hole $V_A$ is opened and the piston body 12 is urged to the rear side by the spring 17. Then, the tubular body 11 is supplied and filled with outside air from the vent hole $V_A$ through the shaft portion vent passage 16. Then, the piston body 12 automatically returns to its original state shown in FIG. 1A. Accordingly, air can be supplied several times in a row by repeatedly pressing the pressing portion 12c.

FIG. 2 and FIG. 3 illustrate a configuration in which the syringe is applied to an endoscope apparatus and water is supplied. In this case, a liquid storage tank (water supply tank) 20 storing a liquid (cleaning water or the like) is attached to the syringe opening 14 of the tubular body 11 through a connecting tube 19 (connecting tube 19 is placed in an upper air layer of the tank). On the one hand, an air supply/water supply tube 23 is provided in the endoscope 22, and an air supply/water supply port 23P is disposed in the operation portion thereof. The air supply/water supply port 23P connects to the tank 20 through the connecting tube 24 (the connecting tube 24 is placed in the liquid). It should be noted that as the air supply/water supply tube 23 and the port 23P, a conventional air supply tube or a water supply tube (3b or 3c) and these ports can be used.

According to such an automatic retractable syringe for an endoscope, in a basic state shown in FIG. 2, when the pressing portion 12c is pressed by a thumb or other finger plugging the vent hole $V_A$ (against the spring 17) as shown in FIG. 3, air is supplied from the syringe opening 14 of the tubular body 11 through the connecting tube 19. Thereby, cleaning water in the tank 20 is supplied to the air supply/water supply tube 23 through the connecting tube 24 and the air supply/water supply port 23P. The cleaning water can be sprayed over the observation window from the air supply/water supply tube 23 through the nozzle on the front end surface of the endoscope to remove contamination and the like of the observation window.

Then, in a state shown in FIG. 3, when the thumb or other finger is released from the pressing portion 12c to release the finger pressure, the vent hole $V_A$ is opened and the piston body 12 is returned to the rear side by the spring 17 as shown in FIG. 2. Then, outside air flows into the tubular body 11 from the vent hole $V_A$ through the shaft portion vent passage 16, and the piston body 12 automatically returns to the basic state. Accordingly, an unlimited amount of water can be supplied several times in a row by repeatedly pressing the pressing portion 12c.

FIG. 4 illustrates a configuration in which the syringe is applied to an endoscope apparatus (device) and air is supplied. In this case, the syringe opening 14 of the tubular body 11 is connected to the air supply/water supply port 26P provided in the endoscope (operation portion) 22. According to such a connection configuration for air supply, in the same manner as for the above described water supply, in a basic state shown in FIG. 4, when the pressing portion 12c is pressed by a thumb or other finger plugging the vent hole $V_A$, air is supplied from the syringe opening 14 through the air supply/water supply port 26P and the air supply/water supply tube 23. As a result, air is sprayed from the nozzle over the observation window to remove water and the like of the observation window.

The present invention can be used to supply air and water consecutively in a medical field and other various kinds of fields.

DESCRIPTION OF SYMBOLS 11 tubular body
12 piston body
12a piston portion (sliding portion)
12b shaft portion
12c pressing portion
syringe (injection) opening
16 shaft portion vent passage
17 spring
19, 24 connecting tube
20 fluid storage tank (water supply tank)
23 air supply/water supply tube
23P, 26P air supply/water supply port
$V_A$ vent hole

What is claimed is:

1. An automatic retractable syringe comprising:
a tubular body on whose front end portion a syringe opening is provided, the syringe opening being an air supply opening;
a piston body in which a vent passage passing from a vent hole of its pressing portion through inside to its front end portion is formed and which reciprocates inside the tubular body, wherein when the pressing portion is pressed by a finger plugging the vent hole, air can be supplied from the syringe opening;
a spring which is disposed between the piston body and the tubular body, and returns the pressed piston body to its original position; and
when the pressing operation of the pressing portion is canceled, the vent hole plugging up with the finger is opened, and the piston body returns to the original position by the spring, and the vent passage takes in the air for air supply into the tubular body, then the piston body sends the air in the tubular body from the syringe opening by the pressing operation of the pressing portion, causing the reciprocation of the piston body;
wherein the syringe opening is pipe-connected to an air supply port of an endoscope or a water supply port of the endoscope or a water supply port of the endoscope through a liquid storage tank.

2. The automatic retractable syringe according to claim 1, wherein the piston body comprises a discoid piston portion which reciprocates in close contact with an inner surface of the tubular body; a rod-shaped shaft portion which supports the piston portion and whose external diameter is smaller than the internal diameter of the tubular body; and a discoid pressing portion which is disposed at a rear side of the shaft portion so as to move back and forth when pressed with a thumb or other finger.

3. The automatic retractable syringe according to claim 1, wherein the spring is provided between a flange portion provided at a rear side of the tubular body and the pressing portion of the piston body.

4. The automatic retractable syringe according to claim 1, wherein the syringe opening is pipe-connected to an air supply port of an endoscope to supply air to the endoscope.

5. The automatic retractable syringe according to claim 4, wherein the syringe opening is pipe-connected to a water supply port of the endoscope through a liquid storage tank to supply water.

* * * * *